United States Patent
Sargeant et al.

(10) Patent No.: US 8,968,785 B2
(45) Date of Patent: Mar. 3, 2015

(54) SURGICAL COMPOSITIONS

(75) Inventors: Timothy Sargeant, Guilford, CT (US); Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 331 days.

(21) Appl. No.: 12/888,456

(22) Filed: Sep. 23, 2010

(65) Prior Publication Data
US 2011/0081417 A1 Apr. 7, 2011

Related U.S. Application Data

(60) Provisional application No. 61/247,998, filed on Oct. 2, 2009.

(51) Int. Cl.
*A61K 9/00* (2006.01)
*A61L 27/52* (2006.01)
*A61L 27/20* (2006.01)
*A61L 27/22* (2006.01)
*A61L 27/24* (2006.01)
*A61L 27/54* (2006.01)

(52) U.S. Cl.
CPC ............. *A61L 27/52* (2013.01); *A61L 27/20* (2013.01); *A61L 27/222* (2013.01); *A61L 27/24* (2013.01); *A61L 27/54* (2013.01); *A61L 2300/252* (2013.01); *A61L 2300/258* (2013.01); *A61L 2300/414* (2013.01); *A61L 2300/64* (2013.01)
USPC ....................................... 424/488; 424/130.1

(58) Field of Classification Search
USPC ................................ 424/488, 130.1
See application file for complete search history.

(56) References Cited

U.S. PATENT DOCUMENTS

| | | | |
|---|---|---|---|
| 4,359,049 A | 11/1982 | Redl et al. | |
| 4,631,055 A | 12/1986 | Redl et al. | |
| 4,735,616 A | 4/1988 | Eibl et al. | |
| 4,874,368 A | 10/1989 | Miller et al. | |
| 4,902,281 A | 2/1990 | Avoy | |
| 4,932,942 A | 6/1990 | Maslanka | |
| 4,978,336 A | 12/1990 | Capozzi et al. | |
| 5,116,315 A | 5/1992 | Capozzi et al. | |
| 5,162,430 A | 11/1992 | Rhee et al. | |
| 5,306,500 A | 4/1994 | Rhee et al. | |
| 5,324,775 A | 6/1994 | Rhee et al. | |
| 5,328,955 A | 7/1994 | Rhee et al. | |
| 5,410,016 A | 4/1995 | Hubbell et al. | |
| 5,514,379 A | 5/1996 | Weissleder et al. | |
| 5,543,441 A | 8/1996 | Rhee et al. | |
| 5,550,187 A | 8/1996 | Rhee et al. | |
| 5,614,587 A | 3/1997 | Rhee et al. | |
| 5,744,545 A | 4/1998 | Rhee et al. | |
| 5,752,974 A | 5/1998 | Rhee et al. | |
| 5,800,541 A | 9/1998 | Rhee et al. | |
| 5,874,500 A | 2/1999 | Rhee et al. | |
| 5,919,455 A | 7/1999 | Greenwald et al. | |
| 5,936,035 A | 8/1999 | Rhee et al. | |
| 6,051,648 A | 4/2000 | Rhee et al. | |
| 6,152,943 A | 11/2000 | Sawhney | |
| 6,165,201 A | 12/2000 | Sawhney et al. | |
| 6,165,489 A | 12/2000 | Berg et al. | |
| 6,179,862 B1 | 1/2001 | Sawhney | |
| 6,514,534 B1 | 2/2003 | Sawhney | |
| 6,534,591 B2 | 3/2003 | Rhee et al. | |
| 6,566,406 B1 | 5/2003 | Pathak et al. | |
| 6,605,294 B2 | 8/2003 | Sawhney | |
| 6,656,200 B2 | 12/2003 | Li et al. | |
| 6,673,093 B1 | 1/2004 | Sawhney | |
| 6,703,047 B2 | 3/2004 | Sawhney et al. | |
| 6,818,018 B1 | 11/2004 | Sawhney | |
| 6,833,408 B2 * | 12/2004 | Sehl et al. ................ 525/54.1 |
| 7,009,034 B2 | 3/2006 | Pathak et al. | |
| 7,176,256 B2 | 2/2007 | Rhee et al. | |
| 7,214,388 B2 | 5/2007 | Harris et al. | |
| 7,223,803 B2 | 5/2007 | Harris et al. | |
| 7,265,186 B2 | 9/2007 | Zhao | |
| 7,316,811 B2 | 1/2008 | Zhao et al. | |
| 7,318,933 B2 | 1/2008 | Hnojewyj | |
| 7,347,850 B2 | 3/2008 | Sawhney | |
| 7,351,787 B2 | 4/2008 | Faure et al. | |
| 7,365,127 B2 | 4/2008 | Wu et al. | |
| 7,435,425 B2 | 10/2008 | Qian et al. | |
| 7,514,541 B2 | 4/2009 | Zhao | |
| 2001/0046476 A1 | 11/2001 | Plochocka | |
| 2003/0108511 A1 | 6/2003 | Sawhney | |
| 2004/0185250 A1 | 9/2004 | John | |
| 2004/0195710 A1 | 10/2004 | Hubbell et al. | |
| 2005/0043814 A1 | 2/2005 | Kusanagi et al. | |

(Continued)

FOREIGN PATENT DOCUMENTS

EP 2 143 737 A1 1/2010
EP 2 196 193 A1 6/2010

(Continued)

OTHER PUBLICATIONS

International Search Report issued in Application EP 11250562.3 mailed Dec. 8, 2011.
International Search Report issued in Application EP 11250564.9 mailed Dec. 8, 2011.
International Search Report issued in Application EP 11250563.1 mailed Dec. 27, 2011.
International Search Report issued in Application EP 11250566.4 mailed Dec. 22, 2011.
International Search Report issued in Application EP 11250565.6 mailed Dec. 23, 2011.
International Search Report from corresponding application EP 10251719.0 mailed May 24, 2013.
Raul Zurita et al.: "Triclosan Release from Coated Polyglycolide Threads", Macromolecular Bioscience, vol. 6, No. 1, Jan. 5, 2006, pp. 58-69.
European Search Report for EP 07751966 date of completion is Nov. 5, 2012.
Extended Search Report from Application No. 11250788.4 dated Aug. 6, 2014.

*Primary Examiner* — Marcia S Noble

(57) ABSTRACT

The present disclosure relates to multi-component hydrogels. The hydrogels may include a natural component having nucleophilic functional groups as well as an electrophilic component. In embodiments, at least one of the components may be branched, having drugs, antibodies, enzymes, and the like incorporated therein, which may react with at least one of the other components of the hydrogel.

22 Claims, No Drawings

(56) References Cited

U.S. PATENT DOCUMENTS

| | | |
|---|---|---|
| 2006/0178475 A1 | 8/2006 | Bentley et al. |
| 2006/0287721 A1* | 12/2006 | Myung et al. .............. 623/5.15 |
| 2007/0032405 A1 | 2/2007 | DeFrees |
| 2007/0203264 A1 | 8/2007 | Harris et al. |
| 2007/0213683 A1 | 9/2007 | Cassingham et al. |
| 2007/0254005 A1 | 11/2007 | Pathak et al. |
| 2007/0292404 A1 | 12/2007 | Walsh et al. |
| 2008/0004421 A1 | 1/2008 | Chenault et al. |
| 2008/0038313 A1 | 2/2008 | Addis et al. |
| 2008/0058246 A1 | 3/2008 | Bhaskaran et al. |
| 2008/0069902 A1 | 3/2008 | Zhao et al. |
| 2008/0108577 A1 | 5/2008 | Hnojewyj |
| 2008/0114092 A1 | 5/2008 | Sawhney |
| 2010/0087854 A1 | 4/2010 | Stopek et al. |

FOREIGN PATENT DOCUMENTS

| | | |
|---|---|---|
| EP | 2 233 160 A2 | 9/2010 |
| EP | 2 233 161 A2 | 9/2010 |
| FR | 2839451 A1 | 11/2003 |
| WO | 2004006961 A1 | 1/2004 |

\* cited by examiner

SURGICAL COMPOSITIONS

CROSS-REFERENCE TO RELATED APPLICATIONS

This application claims the benefit of, and priority to, U.S. Provisional Patent Application Ser. No. 61/247,998 filed on Oct. 2, 2009, the disclosure of which is hereby incorporated by reference in its entirety.

BACKGROUND

The present disclosure relates to hydrogels. Specifically, the disclosure relates to multi-component hydrogels which may include bioactive agents therein.

Biocompatible cross-linked polymers having electrophilic and nucleophilic functional groups are known for their use in the formation of hydrogels. These hydrogels may be used in a variety of surgical applications. Hydrogels may be utilized, for example, as a sealant for wounds, as a glue for adhering surgical implants to tissue, as drug delivery devices, as coatings, combinations thereof, and the like.

Biocompatible polymers, which may be used as tissue scaffolds capable of providing cells with growth and development components, remain desirable.

SUMMARY

The present disclosure provides tissue scaffolds, methods for making same, and methods for using same to repair tissue defects. In embodiments, a tissue scaffold of the present disclosure may include a first hydrogel precursor including a natural component such as collagen, serum, gelatin, hyaluronic acid, and combinations thereof; and a second hydrogel precursor including an electrophilic functional group such as n-hydroxysuccinimides, succinimidyl succinates, succinimidyl propionates, sulfosuccinimides, isocyanates, thiocyanates, carbodiimides, benzotriazole carbonates, and combinations thereof, wherein the first hydrogel precursor and the second hydrogel precursor react to form the tissue scaffold.

Methods of the present disclosure may include, in embodiments, identifying a cartilage defect; cleaning out the cartilage defect; introducing into the defect a first hydrogel precursor including a natural component such as collagen, serum, gelatin, hyaluronic acid, and combinations thereof, in combination with a second hydrogel precursor including n-hydroxysuccinimide electrophilic functional groups, where the second hydrogel precursor may be polyethylene glycol, polyethylene oxide, polyethylene oxide-co-polypropylene oxide, co-polyethylene oxide block or random copolymers, polyvinyl alcohol, poly(vinyl pyrrolidinone), poly(amino acids), dextran, chitosan, alginates, carboxymethylcellulose, oxidized cellulose, hydroxyethylcellulose, hydroxymethylcellulose, hyaluronic acid, albumin, collagen, casein, gelatin, and combinations thereof; and allowing the first hydrogel precursor and the second hydrogel precursor to react to form a hydrogel, wherein the hydrogel forms a tissue scaffold at the site of the cartilage defect.

In a further aspect, the present disclosure provides a first hydrogel precursor including a natural component such as collagen, serum, gelatin, hyaluronic acid, and combinations thereof and a second hydrogel precursor including an electrophilic functional group such as n-hydroxysuccinimides, succinimidyl succinates, succinimidyl propionates, sulfosuccinimides, isocyanates, thiocyanates, carbodiimides, benzotriazole carbonates, and combinations thereof, for use in repairing tissue defects, in particular cartilage defects, wherein the first hydrogel precursor and the second hydrogel precursor react to form a tissue scaffold as described herein.

According to the above aspect of the present disclosure, advantageously the cartilage defect is cleaned out prior to the introduction of the first and/or second hydrogel precursor.

In a further aspect, the present disclosure provides a first hydrogel precursor including a natural component such as collagen, serum, gelatin, hyaluronic acid, and combinations thereof and a second hydrogel precursor including an electrophilic functional group such as n-hydroxysuccinimides, succinimidyl succinates, succinimidyl propionates, sulfosuccinimides, isocyanates, thiocyanates, carbodiimides, benzotriazole carbonates, and combinations thereof, for simultaneous, separate, or sequential administration in repairing tissue defects, in particular cartilage defects, In yet a further aspect, the present disclosure provides a kit for the repair of tissue defects, in particular cartilage defects, which includes a first hydrogel precursor including a natural component such as collagen, serum, gelatin, hyaluronic acid, and combinations thereof and a second hydrogel precursor including an electrophilic functional group such as n-hydroxysuccinimides, succinimidyl succinates, succinimidyl propionates, sulfosuccinimides, isocyanates, thiocyanates, carbodiimides, benzotriazole carbonates, and combinations thereof. In embodiments, the kit according to the present disclosure will also include suitable packaging and/or instructions for use in the repair of tissue defects, in particular cartilage defects.

DETAILED DESCRIPTION

The present disclosure provides hydrogels which include an electrophilic precursor, sometimes referred to herein as an electrophilic crosslinker, and a nucleophilic component. In embodiments, the nucleophilic component is a natural component, which may be cross-linked by the electrophilic crosslinker to form a hydrogel. In embodiments, the hydrogel may be biodegradable. The term "biodegradable" as used herein is defined to include both bioabsorbable and bioresorbable materials. By biodegradable, it is meant that the materials decompose, or lose structural integrity under body conditions (e.g. enzymatic degradation or hydrolysis) or are broken down (physically or chemically) under physiologic conditions in the body such that the degradation products are excretable or absorbable by the body.

The hydrogel may be formed in situ and may be utilized as a drug delivery device or tissue scaffold, combinations thereof, and the like. In embodiments, the hydrogel may deliver and/or release biological factors/molecules and/or cells at the site of implantation. Thus, where the hydrogel of the present disclosure is utilized as a tissue scaffold, it may assist in native tissue regrowth by providing the surrounding tissue with needed nutrients and bioactive agents. In some embodiments, as discussed further below, the hydrogel itself may include a natural component such as collagen, gelatin, hyaluronic acid, combinations thereof, and the like, and thus the natural component may be released at the site of implantation as the hydrogel degrades. The term "natural component" as used herein includes polymers, compositions of matter, materials, combinations thereof, and the like, which can be found in nature or derived from compositions/organisms found in nature. Natural components also may include compositions which are found in nature but can be synthesized by man, for example, using methods to create natural/synthetic/biologic recombinant materials, as well as methods capable of producing proteins with the same sequences as those found in nature, and/or methods capable of producing materials with the same structure and components as natural materials, such as synthetic hyaluronic acid, which is commercially available, for example, from Sigma Aldrich.

The components for forming hydrogels on or in tissues include, for example, in situ forming materials. The in situ forming material may include a single precursor or multiple precursors that form "in situ", meaning formation occurs at a tissue in a living animal or human body. In general, this may be accomplished by having a precursor that can be activated at the time of application to create, in embodiments, a hydrogel. Activation can be through a variety of methods including, but not limited to, environmental changes such as pH, ionicity, temperature, etc. In other embodiments, the components for forming a hydrogel may be contacted outside the body and then introduced into a patient as an implant such as a (pre-formed) tissue scaffold.

As noted above, in situ forming materials may be made from one or more precursors. The precursor may be, e.g., a monomer or a macromer. One type of precursor may have a functional group that is an electrophile or nucleophile. Electrophiles react with nucleophiles to form covalent bonds. Covalent crosslinks or bonds refer to chemical groups formed by reaction of functional groups on different polymers that serve to covalently bind the different polymers to each other. In certain embodiments, a first set of electrophilic functional groups on a first precursor may react with a second set of nucleophilic functional groups on a second precursor. When the precursors are mixed in an environment that permits reaction (e.g., as relating to pH or solvent), the functional groups react with each other to form covalent bonds. The precursors become crosslinked when at least some of the precursors can react with more than one other precursor. For instance, a precursor with two functional groups of a first type may be reacted with a crosslinking precursor that has at least three functional groups of a second type capable of reacting with the first type of functional groups.

In embodiments the hydrogel may be formed from a single precursor or multiple precursors. For example, where the hydrogel is formed from multiple precursors, for example two precursors, the precursors may be referred to as a first and second hydrogel precursor. The terms "first hydrogel precursor" and "second hydrogel precursor" each mean a polymer, functional polymer, macromolecule, small molecule, or crosslinker that can take part in a reaction to form a network of crosslinked molecules, e.g., a hydrogel.

The term "functional group" as used herein refers to electrophilic or nucleophilic groups capable of reacting with each other to form a bond. Electrophilic functional groups include, for example, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In embodiments, the electrophilic functional group is a succinimidyl ester.

The electrophilic hydrogel precursors may have biologically inert and water soluble cores, as well as non-water soluble cores. When the core is a polymeric region that is water soluble, suitable polymers that may be used include: polyethers, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and polyvinyl alcohol ("PVA"); poly(vinyl pyrrolidinone) ("PVP"); poly (amino acids); poly (saccharides), such as dextran, chitosan, alginates, carboxymethylcellulose, oxidized cellulose, hydroxyethylcellulose, hydroxymethylcellulose; hyaluronic acid; and proteins such as albumin, collagen, casein, and gelatin. In embodiments, combinations of the foregoing polymers may be utilized.

The polyethers, and more particularly poly(oxyalkylenes) or poly(ethylene glycol) or polyethylene glycol, may be utilized in some embodiments. When the core is small in molecular nature, any of a variety of hydrophilic functionalities can be used to make the first and second hydrogel precursors water soluble. For example, functional groups like hydroxyl, amine, sulfonate and carboxylate, which are water soluble, may be used to make the precursor water soluble. For example, the n-hydroxysuccinimide ("NHS") ester of subaric acid is insoluble in water, but by adding a sulfonate group to the succinimide ring, the NHS ester of subaric acid may be made water soluble, without affecting its reactivity towards amine groups.

Each of the first and second hydrogel precursors may be multifunctional, meaning that it may include two or more electrophilic or nucleophilic functional groups, such that, for example, a nucleophilic functional group on the first hydrogel precursor may react with an electrophilic functional group on the second hydrogel precursor to form a covalent bond. At least one of the first or second hydrogel precursors includes more than two functional groups, so that, as a result of electrophilic-nucleophilic reactions, the precursors combine to form cross-linked polymeric products.

The macromolecule having the electrophilic functional group may be multi-armed. For example, the macromolecule may be a multi-armed PEG having four, six, eight, or more arms extending from a core. The core may be the same or different from the macromolecule forming the arms. For example, the core may be PEG and the multiple anus may also be PEG. In embodiments, the core may be a natural polymer.

The molecular weight (MW) of the electrophilic crosslinker may be from about 2,000 Daltons (Da) to about 100,000 Da; in embodiments from about 10,000 Da to about 40,000 Da. Multi-arm precursors may have a molecular weight that varies depending on the number of arms. For example, an arm having a 1000 MW of PEG has enough $CH_2CH_2O$ groups to total at least 1000 MW. The combined molecular weight of an individual arm may be from about 250 Da to about 5,000 Da; in embodiments from about 1,000 Da to about 3,000 Da; in embodiments from about 1,250 Da to about 2,500 Da. In embodiments, the electrophilic crosslinker may be a multi-arm PEG functionalized with multiple NHS groups having, for example, four, six or eight arms and a molecular weight from about 5,000 Da to about 25,000 Da. Other examples of suitable precursors are described in U.S. Pat. Nos. 6,152,943; 6,165,201; 6,179,862; 6,514,534; 6,566,406; 6,605,294; 6,673,093; 6,703,047; 6,818,018; 7,009,034; and 7,347,850, the entire disclosures of each of which are incorporated herein by reference.

The electrophilic precursor may be a cross-linker that provides an electrophilic functional group capable of bonding with nucleophiles on another component, in embodiments a natural component. The natural component may be endogenous to the patient to which the electrophilic crosslinker is applied, or may be exogenously applied.

In embodiments, one of the precursors may be a natural component possessing nucleophilic groups. Nucleophilic groups which may be present include, for example, $—NH_2$, $—SH$, $—OH$, $—PH_2$, and $—CO—NH—NH_2$.

The natural component may be, for example, collagen, gelatin, blood (including serum, which may be whole serum or extracts therefrom), hyaluronic acid, proteins, albumin, other serum proteins, serum concentrates, platelet rich plasma (prp), combinations thereof, and the like. Additional suitable natural components which may be utilized or added to another natural component, sometimes referred to herein as a bioactive agent, include, for example, stem cells, DNA, RNA, enzymes, growth factors, peptides, polypeptides, antibodies, other nitrogenous natural molecules, combinations thereof, and the like. Other natural components may include derivatives of the foregoing, for example modified hyaluronic acid, dextran, other polysaccharide, polymers and/or polypeptides, including aminated polysaccharides which may be naturally derived, synthetic, or biologically derived. For example, in embodiments hyaluronic acid may be modified to make it nucleophilic.

In embodiments, any of the above natural components may be synthetically prepared, e.g., synthetic hyaluronic acid, utilizing methods within the purview of those skilled in the art. Similarly, in embodiments the natural component could be a natural or synthetic long chain aminated polymer. The natural component may also be modified, i.e., aminated to create a nucleophilic polymer.

The natural component may provide cellular building blocks or cellular nutrients to the tissue that it contacts in situ. For example, serum contains proteins, glucose, clotting factors, mineral ions, and hormones which may be useful in the formation or regeneration of tissue.

In embodiments, the natural component includes whole serum. In embodiments, the natural component is autologous, i.e., collagen, serum, blood, and the like, from the body where the hydrogel is (or is to be) formed. In this manner, the person or animal in which the hydrogel is to be used may provide the natural component for use in formation of the hydrogel. In such embodiments, the resulting hydrogel is semi-autologous, including a synthetic electrophilic precursor and an autologous/endogenous nucleophilic precursor.

In embodiments, a multifunctional nucleophilic polymer, such as a natural component having multiple amine groups, may be used as a first hydrogel precursor and a multifunctional electrophilic polymer, such as a multi-arm PEG functionalized with multiple NHS groups, may be used as a second hydrogel precursor. In embodiments, the precursors may be in solution(s), which may be combined to permit formation of the hydrogel. Any solutions utilized as part of the in situ forming material system should not contain harmful or toxic solvents. In embodiments, the precursor(s) may be substantially soluble in a solvent such as water to allow application in a physiologically-compatible solution, such as buffered isotonic saline.

In embodiments, a hydrogel may be formed from a combination of collagen and gelatin as the natural component, with a multi-functional PEG utilized as a crosslinker. In embodiments, the collagen or gelatin may be placed in solution, utilizing a suitable solvent. Such a buffer may have a pH from about 8 to about 12, in embodiments from about 8.2 to about 9. Examples of such buffers include, but are not limited to, borate buffers, and the like.

In a second solution, an electrophilic crosslinker, in embodiments a multi-arm PEG functionalized with electrophilic groups such as n-hydroxysuccinimide, may be prepared in a buffer such as Hanks Balanced Salt Solution, Dulbecco's Modified Eagle's Medium, Phosphate Buffered Saline, water, phosphate buffer, combinations thereof, and the like. The electrophilic crosslinker, in embodiments a multi-arm PEG functionalized with n-hydroxysuccinimide groups, may be present in a solution including the above buffer at a concentration from about 0.02 grams/ml to about 0.5 grams/ml, in embodiments from about 0.05 grams/ml to about 0.3 grams/ml.

The two components may be introduced in situ, wherein the electrophilic groups on the multi-arm PEG crosslink the amine nucleophilic components of the collagen and/or gelatin. The ratio of natural component to electrophilic component (i.e., collagen:PEG) may be from about 0.1:1 to about 100:1, in embodiments from about 1:1 to about 10:1.

The natural components, e.g., collagen, gelatin, and/or hyaluronic acid, may together be present at a concentration of at least about 1.5 percent by weight of the hydrogel, in embodiments from about 1.5 percent by weight to about 20 percent by weight of the hydrogel, in other embodiments from about 2 percent by weight to about 10 percent by weight of the hydrogel. In certain embodiments, collagen may be present from about 0.5 percent to about 7 percent by weight of the hydrogel, in further embodiments, from about 1 percent to about 4 percent by weight of the hydrogel. In another embodiment, gelatin may be present from about 1 percent to about 20 percent by weight of the hydrogel, in further embodiments, from about 2 percent to about 10 percent by weight of the hydrogel. In yet another embodiment, hyaluronic acid and collagen combined as the natural component(s) may be present from about 0.5 percent to about 8 percent by weight of the hydrogel, in further embodiments, from about 1 percent to about 5 percent by weight of the hydrogel. It is also envisioned that the hyaluronic acid may not be present as a "structural" component, but as more of a bioactive agent. For example, hyaluronic acid may be present in solution/gel in concentrations as low as 0.001 percent by weight of the solution/gel and have biologic activity.

The electrophilic crosslinker may be present in amounts of from about 0.5 percent by weight to about 20 percent by weight of the hydrogel, in embodiments from about 1.5 percent by weight to about 15 percent by weight of the hydrogel.

In situ forming materials may be formed either through covalent, ionic or hydrophobic bonds. Physical (non-covalent) crosslinks may result from complexation, hydrogen bonding, desolvation, Van der Waals interactions, ionic bonding, combinations thereof, and the like, and may be initiated by mixing two precursors that are physically separated until combined in situ, or as a consequence of a prevalent condition in the physiological environment, including: temperature, pH, ionic strength, combinations thereof, and the like. Chemical (covalent) crosslinking may be accomplished by any of a number of mechanisms, including: free radical polymerization, condensation polymerization, anionic or cationic polymerization, step growth polymerization, electrophile-nucleophile reactions, combinations thereof, and the like.

In some embodiments, in situ forming material systems may include biocompatible multi-precursor systems that spontaneously crosslink when the precursors are mixed, but wherein the two or more precursors are individually stable for the duration of the deposition process. In other embodiments, in situ forming materials may include a single precursor that crosslinks with endogenous materials and/or tissues.

The crosslinking density of the resulting biocompatible crosslinked polymer may be controlled by the overall molecular weight of the crosslinker and natural component and the number of functional groups available per molecule. A lower molecular weight between crosslinks, such as 600 Da, will give much higher crosslinking density as compared to a higher molecular weight, such as 10,000 Da. Elastic gels may be obtained with higher molecular weight natural components with molecular weights of more than 3000 Da.

The crosslinking density may also be controlled by the overall percent solids of the crosslinker and natural component solutions. Increasing the percent solids increases the probability that an electrophilic group will combine with a nucleophilic group prior to inactivation by hydrolysis. Yet another method to control crosslink density is by adjusting the stoichiometry of nucleophilic groups to electrophilic groups. A one to one ratio may lead to the highest crosslink density, however, other ratios of reactive functional groups (e.g., electrophile:nucleophile) are envisioned to suit a desired formulation.

The natural component containing a nucleophilic functional group and the electrophilic functional precursor react to form a hydrogel. The reaction may occur in situ or outside of the body for future implantation therein or thereon. In embodiments, a hydrogel of the present disclosure may be produced by combining precursors that crosslink quickly after application to a surface, e.g., on a tissue of a patient, to form an in situ forming material.

The hydrogel thus produced may be bioabsorbable, so that it does not have to be retrieved from the body. Absorbable materials are absorbed by biological tissues and disappear in vivo at the end of a given period, which can vary, for example, from one day to several months, depending on the chemical nature of the material. Absorbable materials include both natural and synthetic biodegradable polymers, as well as bioerodible polymers.

In embodiments, one or more precursors having biodegradable linkages present in between functional groups may be included to make the hydrogel biodegradable or absorbable. In some embodiments, these linkages may be, for example, esters, which may be hydrolytically degraded in physiological solution. The use of such linkages is in contrast to protein linkages that may be degraded by proteolytic action. A biodegradable linkage optionally also may form part of a water soluble core of one or more of the precursors. Alternatively, or in addition, functional groups of precursors may be chosen such that the product of the reaction between them results in a biodegradable linkage. For each approach, biodegradable linkages may be chosen such that the resulting biodegradable biocompatible crosslinked polymer degrades or is absorbed in a desired period of time. Generally, biodegradable linkages may be selected that degrade the hydrogel under physiological conditions into non-toxic or low toxicity products.

The gels of the present disclosure may degrade due to hydrolysis or enzymatic degradation of the biodegradable region, whether part of the natural component or introduced into a synthetic electrophilic crosslinker. The degradation of gels containing synthetic peptide sequences will depend on the specific enzyme and its concentration. In some cases, a specific enzyme may be added during the crosslinking reaction to accelerate the degradation process. In the absence of any degradable enzymes, the crosslinked polymer may degrade solely by hydrolysis of the biodegradable segment. In embodiments in which polyglycolate is used as the biodegradable segment, the crosslinked polymer may degrade in from about 1 day to about 30 days depending on the crosslinking density of the network. Similarly, in embodiments in which a polycaprolactone based crosslinked network is used, degradation may occur over a period of time from about 1 month to about 8 months. The degradation time generally varies according to the type of degradable segment used, in the following order: polyglycolate<polylactate<polytrimethylene carbonate<polycaprolactone. Thus, it is possible to construct a hydrogel with a desired degradation profile, from a few days to months, using a proper degradable segment.

Where utilized, the hydrophobicity generated by biodegradable blocks such as oligohydroxy acid blocks or the hydrophobicity of PPO blocks in PLURONIC™ or TETRONIC™ polymers utilized to form the electrophilic crosslinker may be helpful in dissolving small organic drug molecules. Other properties which will be affected by incorporation of biodegradable or hydrophobic blocks include: water absorption, mechanical properties and thermosensitivity.

Properties of the in situ forming material system may be selected according to the intended application. For example, if the in situ forming material is to be used to temporarily occlude a reproductive organ, such as a fallopian tube, it may be desirable that the in situ forming material system undergo significant swelling and be biodegradable. Alternatively, the in situ forming material may have thrombotic properties, or its precursors may react with blood or other body fluids to form a coagulum. In embodiments, the precursors react with blood or body fluids, which may be endogenous or exogenously applied, thereby forming a tissue scaffold.

Other applications may require different characteristics of the in situ forming material system. Generally, the materials should be selected on the basis of exhibited biocompatibility and lack of toxicity.

Certain properties of the in situ forming material can be useful, including adhesion to a variety of tissues, desirable setting times to enable a surgeon to accurately and conveniently place the in situ forming materials, high water content for biocompatibility, which may be relevant for hydrogels, mechanical strength for use in sealants, and/or toughness to resist destruction after placement. Synthetic materials that are readily sterilized and avoid the dangers of disease transmission involved in the use of natural materials may thus be used. Indeed, certain in situ polymerizable hydrogels made using synthetic precursors are within the purview of those skilled in the art, e.g., as used in commercially available products such as FOCALSEAL® (Genzyme, Inc.), COSEAL® (Angiotech Pharmaceuticals), and DURASEAL® (Confluent Surgical, Inc). Other known hydrogels include, for example, those disclosed in U.S. Pat. Nos. 6,656,200; 5,874,500; 5,543,441; 5,514,379; 5,410,016; 5,162,430; 5,324,775; 5,752,974; and 5,550,187.

As noted above, in embodiments a branched multi-arm PEG, sometimes referred to herein as a PEG star, may be included to form a hydrogel of the present disclosure. A PEG star may be functionalized so that its arms include biofunctional groups such as amino acids, peptides, antibodies, enzymes, drugs, combinations thereof, or other moieties such as bioactive agents in its cores, its arms, or at the ends of its arms. The biofunctional groups may also be incorporated into the backbone of the PEG, or attached to a reactive group contained within the PEG backbone. The binding can be covalent or non-covalent, including electrostatic, thiol mediated, peptide mediated, or using known reactive chemistries, for example, biotin with avidin.

Amino acids incorporated into a PEG star may be natural or synthetic, and can be used singly or as part of a peptide. Sequences may be utilized for cellular adhesion, cell differentiation, combinations thereof, and the like, and may be useful for binding other biological molecules such as growth factors, drugs, cytokines, DNA, antibodies, enzymes, combinations thereof, and the like. Such amino acids may be released upon enzymatic degradation of the PEG star.

These PEG stars may also include functional groups as described above to permit their incorporation into a hydrogel. The PEG star may be utilized as the electrophilic crosslinker or, in embodiments, be utilized as a separate component in addition to the electrophilic crosslinker described above. In embodiments, the PEG stars may include electrophilic groups that bind to nucleophilic groups. As noted above, the nucleophilic groups may be part of a natural component utilized to form a hydrogel of the present disclosure.

In some embodiments a biofunctional group may be included in a PEG star by way of a degradable linkage, including an ester linkages formed by the reaction of PEG carboxylic acids or activated PEG carboxylic acids with alcohol groups on a biofunctional group. In this case, the ester groups may hydrolyze under physiological conditions to release the biofunctional group.

In embodiments an in situ forming material may also include an initiator. An initiator may be any precursor or group capable of initiating a polymerization reaction for the formation of the in situ forming material.

In Situ Polymerization

The precursor(s) may be dissolved to form a solution prior to use, with the solution being delivered to the patient. As used herein, a solution may be homogeneous, heterogeneous, phase separated, or the like. In other embodiments, the precursor(s) may be in an emulsion. Solutions suitable for use in accordance with the present disclosure include those that may be used to form implants in lumens or voids. Where two solutions are employed, each solution may contain one precursor of an in situ forming material which forms upon contact. The solutions may be separately stored and mixed when delivered to tissue.

Electrophilic crosslinkers as described above may be reacted with natural components to generate crosslinked polymeric networks. Generally, aqueous solutions of crosslinkers may be mixed with natural components to produce a crosslinked hydrogel. The reaction conditions for forming a crosslinked polymeric hydrogel will depend on the nature of the functional groups. In embodiments, reactions are conducted in buffered aqueous solutions at a pH of about 5 to about 12. Buffers include, for example, phosphate buffered saline (PBS), Hanks Balanced Salt Solution, Dulbecco's Modified Eagle's Medium, water, phosphate buffer, sodium borate buffer, triethanol amine buffer, combinations thereof, and the like. In some embodiments, organic solvents such as ethanol or isopropanol may be added to improve the reaction speed or to adjust the viscosity of a given formulation.

When the electrophilic crosslinker is synthetic (for example, based on polyalkylene oxide), it may be desirable to use molar equivalent quantities of the reactants. In some cases, molar excess of an electrophilic crosslinker may be added to compensate for side reactions such as reactions due to hydrolysis of the functional group.

When choosing the electrophilic crosslinker and natural component, at least one of the precursors may have more than two functional groups per molecule and at least one degradable region, if it is desired that the resultant biocompatible crosslinked polymer be biodegradable.

Formulations may be prepared that are suited to make precursor crosslinking reactions occur in situ. In general, this may be accomplished by having a precursor that can be activated at the time of application to a tissue to form a crosslinked hydrogel. Activation can be made before, during, or after application of the precursor to the tissue, provided that the precursor is allowed to conform to the tissue's shape before crosslinking and associated gelation is otherwise too far advanced. Activation includes, for instance, mixing precursors with functional groups that react with each other. Thus, in situ polymerization includes activation of chemical moieties to form covalent bonds to create an insoluble material, e.g., a hydrogel, at a location where the material is to be placed on, within, or both on and within, a patient. In situ polymerizable polymers may be prepared from precursor(s) that can be reacted such that they form a polymer within the patient. Thus precursor(s) with electrophilic functional groups can be mixed or otherwise activated in the presence of precursors with nucleophilic functional groups.

With respect to coating a tissue, and without limiting the present disclosure to a particular theory of operation, it is believed that reactive precursor species that crosslink quickly after contacting a tissue surface may form a three dimensional structure that is mechanically interlocked with the coated tissue. This interlocking contributes to adherence, intimate contact, and continuous coverage of the coated region of the tissue. In other embodiments, where electrophilic precursors are used, such precursors may react with free amines in tissue, thereby serving as a means for attaching the hydrogel to tissue.

The crosslinking reaction leading to gelation can occur, in some embodiments within a time from about 1 second to about 5 minutes, in embodiments from about 3 seconds to about 1 minute; persons of ordinary skill in these arts will immediately appreciate that all ranges and values within these explicitly stated ranges are contemplated. For example, in embodiments, the in situ gelation time of hydrogels according to the present disclosure is less than about 20 seconds, and in some embodiments, less than about 10 seconds, and in yet other embodiments less than about 5 seconds.

Administration

As noted above, the electrophilic crosslinker may be introduced by itself, whereby it crosslinks endogenous natural components. Alternatively, natural components may be removed from a patient or obtained from other sources, and then introduced along with the electrophilic crosslinker to form a hydrogel of the present disclosure, such as, for example, plasma. The precursor(s) may be placed into solution prior to use, with the solution being delivered to the patient. One may use a syringe for delivery of a single precursor, i.e., an electrophilic crosslinker, or a dual syringe or similar device to apply more than one precursor solutions, such as those described in U.S. Pat. Nos. 4,874,368; 4,631, 055; 4,735,616; 4,359,049; 4,978,336; 5,116,315; 4,902,281; 4,932,942; 6,179,862; 6,673,093; and 6,152,943.

In other embodiments, the precursors may be combined to create a film or foam, which then may be inplanted into the patient. Methods for creating films and foams are within the purview those skilled in the art, which include but are not limited to spraying, film casting, lyophilization techniques, etc.

Uses

As noted above, the hydrogels of the present disclosure may be utilized as tissue adhesives or sealants. The hydrogel may also be used to correct a tissue defect. As used herein, a "tissue defect" may include any breakdown of tissue from a normal, healthy state. This breakdown may be due to internal factors such as degenerative disease, or external factors such as injury. Any variation from the normal structure of a tissue may be a "tissue defect." In some embodiments, where utilized to correct a tissue defect, a hydrogel of the present disclosure may be referred to as a tissue scaffold.

The hydrogel compositions may be utilized for cartilage repair, tendon repair, ligament repair, treatment of osteoarthritis, bone fillers, to repair soft tissue defects, as a filler for soft/hard tissue interfaces, and/or for general organ or tissue repair. General organ or tissue repair may include, for example, gastrointestinal, thoracic, cardiac, neural, or other organ repair.

In embodiments, where utilized for cartilage repair, a method for using a hydrogel of the present disclosure may include identifying a cartilage defect and then cleaning out the cartilage defect. Once the defect has been cleaned, a hydrogel composition of the present disclosure may be introduced into the defect. As noted above, in embodiments, at least one hydrogel precursor may be introduced therein. In embodiments, one of the precursors, sometimes referred to as a first hydrogel precursor, may be a natural component possessing nucleophilic groups. As noted above, the natural component may be endogenous or exogenously applied. A second precursor possessing electrophilic functional groups may also be applied to the defect utilizing any method or apparatus described above or as within the purview of those skilled in the art. The first hydrogel precursor and the second hydrogel precursor may then be allowed to react to form a hydrogel, which may act as a tissue scaffold at the site of the cartilage defect.

The hydrogel may be porous or smooth. In certain embodiments, the hydrogel may be porous. The term "porous" as used herein means that the hydrogel may possess defined openings and/or spaces which are present as a surface characteristic or a bulk material property, partially or completely penetrating the hydrogel. Pores may be created using methods within the purview of those skilled in the art including, but not limited to, processes such as sintering, leaching of salt, sugar or starch crystals. Porous materials may have an open-cell structure, where the pores are connected to each other, forming an interconnected network. Conversely, hydrogel may be closed cell, where the pores are not interconnected.

The hydrogel may be coated with or include additional bioactive agents. The term "bioactive agent", as used herein, is used in its broadest sense and includes any substance or mixture of substances that have clinical use. Consequently, bioactive agents may or may not have pharmacological activity per se, e.g., a dye.

Alternatively a bioactive agent could be any agent which provides a therapeutic or prophylactic effect, a compound that affects or participates in tissue growth, cell growth, cell differentiation, an anti-adhesive compound, a compound that may be able to invoke a biological action such as an immune response, or could play any other role in one or more biological processes. It is envisioned that the bioactive agent may be applied to the hydrogel in any suitable form of matter, e.g., films, powders, liquids, gels and the like.

As noted above, in embodiments that include a multi-arm PEG or PEG star, the bioactive agent may be incorporated into the core of the PEG, the arms of the PEG, or combinations thereof. In embodiments, the bioactive agent may be attached to a reactive group in the PEG chain. The bioactive agent may be bound covalently, non-covalently, i.e., electrostatically, through a thiol-mediated or peptide-mediated bond, or using biotin-avidin chemistries and the like.

Examples of classes of bioactive agents, which may be utilized in accordance with the present disclosure include, for example, anti-adhesives, antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, platelet activating drugs, clotting factors and enzymes. It is also intended that combinations of bioactive agents may be used.

Anti-adhesive agents can be used to prevent adhesions from forming between the hydrogel and the surrounding tissues opposite the target tissue. In addition, anti-adhesive agents may be used to prevent adhesions from forming between the coated implantable medical device and the packaging material. Some examples of these agents include, but are not limited to hydrophilic polymers such as poly(vinyl pyrrolidone), carboxymethyl cellulose, hyaluronic acid, polyethylene oxide, poly vinyl alcohols, and combinations thereof.

Suitable antimicrobial agents which may be included as a bioactive agent include, for example, triclosan, also known as 2,4,4'-trichloro-2'-hydroxydiphenyl ether, chlorhexidine and its salts, including chlorhexidine acetate, chlorhexidine gluconate, chlorhexidine hydrochloride, and chlorhexidine sulfate, silver and its salts, including silver acetate, silver benzoate, silver carbonate, silver citrate, silver iodate, silver iodide, silver lactate, silver laurate, silver nitrate, silver oxide, silver palmitate, silver protein, and silver sulfadiazine, polymyxin, tetracycline, aminoglycosides, such as tobramycin and gentamicin, rifampicin, bacitracin, neomycin, chloramphenicol, miconazole, quinolones such as oxolinic acid, norfloxacin, nalidixic acid, pefloxacin, enoxacin and ciprofloxacin, penicillins such as oxacillin and pipracil, nonoxynol 9, fusidic acid, cephalosporins, and combinations thereof. In addition, antimicrobial proteins and peptides such as bovine lactoferrin and lactoferricin B may be included as a bioactive agent.

Other bioactive agents, which may be included as a bioactive agent include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents, such as coronary vasodilators and nitroglycerin; alkaloids; analgesics; narcotics such as codeine, dihydrocodeinone, meperidine, morphine and the like; non-narcotics, such as salicylates, aspirin, acetaminophen, d-propoxyphene and the like; opioid receptor antagonists, such as naltrexone and naloxone; anti-cancer agents; anti-convulsants; anti-emetics; antihistamines; anti-inflammatory agents, such as hormonal agents, hydrocortisone, prednisolone, prednisone, non-hormonal agents, allopurinol, indomethacin, phenylbutazone and the like; prostaglandins and cytotoxic drugs; chemotherapeutics, estrogens; antibacterials; antibiotics; anti-fungals; anti-virals; anticoagulants; anticonvulsants; antidepressants; antihistamines; and immunological agents.

Other examples of suitable bioactive agents, which may be included in the hydrogel include, for example, viruses and cells, including stem cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, α-IFN and γ-IFN); erythropoietin; nucleases; tumor necrosis factor; colony stimulating factors (e.g., GCSF, GM-CSF, MCSF); insulin; anti-tumor agents and tumor suppressors; blood proteins such as fibrin, thrombin, fibrinogen, synthetic thrombin, synthetic fibrin, synthetic fibrinogen; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); bone morphogenic proteins; TGF-B; protein inhibitors; protein antagonists; protein agonists; nucleic acids, such as antisense molecules, DNA, RNA, RNAi; oligonucleotides; polynucleotides; and ribozymes.

The precursors and/or the hydrogel formed from the precursors may contain visualization agents to improve their visibility during surgical procedures. Visualization agents may be selected from a variety of non-toxic colored substances, such as dyes, suitable for use in implantable medical devices. Suitable dyes are within the purview of those skilled in the art and may include, for example, a dye for visualizing a thickness of the hydrogel as it is formed in situ, e.g., as described in U.S. Pat. No. 7,009,034. In some embodiments, a suitable dye may include, for example, FD&C Blue #1, FD&C Blue #2, FD&C Blue #3, FD&C Blue #6, D&C Green #6, methylene blue, indocyanine green, other colored dyes, and combinations thereof. It is envisioned that additional visualization agents may be used such as fluorescent compounds (e.g., flurescein or eosin), x-ray contrast agents (e.g., iodinated compounds), ultrasonic contrast agents, and MRI contrast agents (e.g., Gadolinium containing compounds).

The visualization agent may be present in either a crosslinker or natural component solution. The colored substance may or may not become incorporated into the resulting hydrogel. In embodiments, however, the visualization agent does not have a functional group capable of reacting with the crosslinker or natural component.

The visualization agent may be used in small quantities, in embodiments less than 1% weight/volume, and in other embodiments less that 0.01% weight/volume and in yet other embodiments less than 0.001% weight/volume concentration.

In embodiments, the bioactive agent may be encapsulated by the hydrogel. For example, the hydrogel may form polymer microspheres around the bioactive agent.

Where the hydrogel is utilized as a tissue scaffold, it may be desirable to include bioactive agents which promote wound healing and/or tissue growth, including colony stimulating factors, blood proteins, fibrin, thrombin, fibrinogen, hormones and hormone analogs, blood coagulation factors, growth factors, bone morphogenic proteins, TGF-β, IGF, combinations thereof, and the like.

As the hydrogel hydrolyzes in situ, the bioactive components and any added bioactive agents are released. This may provide nutrients from the natural components, as well as bioactive agents, to the surrounding tissue, thereby promoting growth and/or regeneration of tissue.

The following Examples are being submitted to illustrate embodiments of the present disclosure. These Examples are intended to be illustrative only and are not intended to limit the scope of the present disclosure. Also, parts and percentages are by weight unless otherwise indicated.

EXAMPLES

Example 1

A hydrogel is prepared as follows. Collagen is dissolved in borate buffer (pH 8.75) using a sonicator at about 37° C. for approximately 5 minutes to yield a final concentration of from about 3 to about 6% by weight. The collagen solution is then centrifuged to remove gas/bubbles. Separately, a multi-arm PEG is dissolved in Hanks buffer (at a neutral pH) to yield a final concentration of from about 4 to about 40% by weight. The two solutions are then simultaneously sprayed in situ at a 1:1 ratio to yield a final gel concentration of from about 1.5 to about 3% by weight collagen, and from about 2.5 to about 20% by weight PEG.

Example 2

A hydrogel is prepared as set forth in Example 1, except at a 10:1 ratio collagen:PEG, to yield a final gel concentration of from about 0.5 to about 4% by weight multiarm PEG and from about 3 to about 6% by weight collagen.

Example 3

A hydrogel is prepared as follows. Gelatin is dissolved at a concentration of from about 5 to about 15% by weight in borate buffer at a pH of about 8.25. Separately, a multi-arm PEG is dissolved in Hanks buffer at a concentration of from about 5 to about 20% by weight. Solutions are simultaneously sprayed in situ at a 1:1 ratio, yielding a final gel concentration of from about 2.5 to about 7.5% by weight gelatin, and from about 2.5 to about 10% by weight multi-armed PEG.

Example 4

A hydrogel is prepared as follows. Hyaluronic acid is dissolved in Hanks buffer at neutral pH, at up to about 2% by weight. A multi-arm PEG is next added to the hyaluronic acid solution at a concentration of from about 5 to about 20% by weight. In a separate vessel, collagen is dissolved in a borate buffer (pH 8.75) at a final solution concentration of from about 3 to about 6% by weight. The 2 solutions are then sprayed at a 1:1 ratio in situ. The final gel concentration is about 1% by weight hyaluronic acid, from about 1.5 to about 3% by weight collagen, and from about 2.5 to about 10% by weight multi-arm PEG.

The components of the gels of Examples 1, 3 and 4 are summarized below in Table 1.

TABLE 1

| | | In Situ Forming Hydrogel Formulations and Conditions | | | |
|---|---|---|---|---|---|
| Example | Material | Component 1 Composition Range | Component 2 Composition Range | pH | Buffers |
| 1 | Multi-armed PEG & Collagen | PEG: 4a10kSS, 4a20kSG, 8a15kSG; 0.0239-0.3828 g/mL | Collagen: bovine type I; 2-6 wt % | PEG in water or saline; Collagen pH ≥ 8 | Hanks, PBS, DPBS, cell culture media |
| 3 | Multi-armed PEG & Gelatin | PEG: 4a10kSS, 4a20kSG, 8a15kSG; 0.0239-0.3828 g/mL | Gelatin: bovine type B; 5-20 wt % | PEG in water or saline; Gelatin pH ≥ 8 | Hanks, PBS, DPBS, cell culture media |

TABLE 1-continued

In Situ Forming Hydrogel Formulations and Conditions

| Example | Material | Component 1 Composition Range | Component 2 Composition Range | pH | Buffers |
|---------|----------|-------------------------------|-------------------------------|-----|---------|
| 4 | Multi-armed PEG & Collagen & Hyaluronan | PEG: 4a20kSG, 8a15kSG; 0.0239-0.3828 g/mL | Collagen: bovine type I; 2-6 wt % HA: 74, 130, 770, 910 kDa; up to 2 wt % | PEG in water or saline; Collagen pH ≥ 8 | Hanks, PBS, DPBS, cell culture media |

4a10kSS: 4 arm PEG; Molecular weight (Mw) 10 kDa; SS (succinimidyl succinate)linker
4a20kSG: 4 arm PEG; Mw 20 kDa; SG (succinimidyl glutarate) linker
8a15kSG: 8 arm PEG; Mw 15 kDa; SG linker
*Note,
concentrations are for each component prior to mixing at 1:1

It should be noted that while the examples listed above are formed in situ, the materials may be formed ex vivo and then utilized as an implant in situ.

While the above description contains many specifics, these specifics should not be construed as limitations on the scope of the present disclosure, but merely as exemplifications of preferred embodiments thereof. Those skilled in the art will envision many other possible variations that are within the scope and spirit of the present disclosure.

What is claimed is:

1. A tissue scaffold comprising:
   a first hydrogel precursor comprising a natural component selected from the group consisting of collagen, serum, gelatin, hyaluronic acid, and combinations thereof;
   a second hydrogel precursor comprising an electrophilic functional group selected from the group consisting of n-hydroxysuccinimides, succinimidyl succinates, succinimidyl propionates, sulfosuccinimides, isocyanates, thiocyanates, carbodiimides, benzotriazole carbonates, and combinations thereof; and
   at least one multi-armed polyethylene glycol functionalized with a component selected from the group consisting of bioactive agents, antibodies, enzymes, and combinations thereof,
   wherein the first hydrogel precursor and the second hydrogel precursor react to form the tissue scaffold.

2. The tissue scaffold of claim 1, wherein the natural component includes a nucleophilic functional group.

3. The tissue scaffold of claim 1, wherein the first hydrogel precursor is exogenous to a patient.

4. The tissue scaffold of claim 1, wherein the first hydrogel precursor is endogenous to a patient.

5. The tissue scaffold of claim 1, wherein the second hydrogel precursor comprises a polyethylene glycol having n-hydroxysuccinimide groups.

6. The tissue scaffold of claim 1, wherein the at least one multi-armed polyethylene glycol comprises the second hydrogel precursor.

7. The tissue scaffold of claim 6, wherein the at least one multi-armed polyethylene glycol has four arms.

8. The tissue scaffold of claim 1, wherein the first hydrogel precursor is present in an amount from about 1.5 to about 20 percent by weight of the tissue scaffold, and the second hydrogel precursor is present in an amount from about 0.5 to about 20 percent by weight of the tissue scaffold.

9. The tissue scaffold of claim 1, wherein the tissue scaffold further comprises at least one additional bioactive agent selected from the group consisting of stem cells, DNA, RNA, enzymes, growth factors, peptides, polypeptides, antibodies, and combinations thereof.

10. A method comprising:
    identifying a cartilage defect;
    cleaning out the cartilage defect;
    introducing into the defect a first hydrogel precursor comprising a natural component selected from the group consisting of collagen, serum, gelatin, hyaluronic acid, and combinations thereof; a second hydrogel precursor comprising an electrophilic functional group selected from the group consisting of n-hydroxysuccinimides, succinimidyl succinates, succinimidyl propionates, sulfosuccinimides, isocyanates, thiocyanates, carbodiimides, benzotriazole carbonates, and combinations thereof; and at least one multi-armed polyethylene glycol functionalized with a component selected from the group consisting of bioactive agents, antibodies, enzymes, and combinations thereof;
    allowing the first hydrogel precursor and the second hydrogel precursor to react to form a hydrogel,
    wherein the hydrogel forms a tissue scaffold at the site of the cartilage defect.

11. The method of claim 10, wherein the first hydrogel precursor is exogenously applied to the defect.

12. The method of claim 10, wherein the first hydrogel precursor is endogenous to the defect and the hydrogel is semi-autologous.

13. The method of claim 10, wherein the natural component is whole serum.

14. The method of claim 10, wherein the second hydrogel precursor comprises a polyethylene glycol having n-hydroxysuccinimide groups.

15. The method of claim 14, wherein the polyethylene glycol having n-hydroxysuccinimide groups has multiple arms.

16. The method of claim 15, wherein the polyethylene glycol having n-hydroxysuccinimide groups has four arms.

17. The method of claim 10, wherein the first hydrogel precursor is present in an amount from about 1.5 to about 20 percent by weight of the hydrogel, and the second hydrogel precursor is present in an amount from about 0.5 to about 20 percent by weight of the hydrogel.

18. The method of claim 10, wherein the hydrogel further comprises at least one bioactive agent selected from the group consisting of stem cells, DNA, RNA, enzymes, growth factors, peptides, polypeptides, antibodies, and combinations thereof.

19. The method of claim 10, wherein the first hydrogel precursor and the second hydrogel precursor are simultaneously applied to the defect.

20. The method of claim 10, wherein the first hydrogel precursor and the second hydrogel precursor are separately applied to the defect.

21. The method of claim 10, wherein the first hydrogel precursor and the second hydrogel precursor are sequentially applied to the defect.

22. A kit for the repair of tissue defects comprising:
- a first hydrogel precursor comprising a natural component selected from the group consisting of collagen, serum, gelatin, hyaluronic acid, and combinations thereof;
- a second hydrogel precursor comprising an electrophilic functional group selected from the group consisting of n-hydroxysuccinimides, succinimidyl succinates, succinimidyl propionates, sulfosuccinimides, isocyanates, thiocyanates, carbodiimides, benzotriazole carbonates, and combinations thereof; and
- at least one multi-armed polyethylene glycol functionalized with a component selected from the group consisting of bioactive agents, antibodies, enzymes, and combinations thereof.

* * * * *